United States Patent
De Faveri et al.

(10) Patent No.: US 11,384,056 B2
(45) Date of Patent: Jul. 12, 2022

(54) METHOD FOR THE MANUFACTURING OF DELMOPINOL INTERMEDIATES

(71) Applicant: Lundbeck Pharmaceuticals Italy S.p.A., Padua (IT)

(72) Inventors: Carla De Faveri, Farra di Soligo (IT); Mariano Stivanello, Schio (IT)

(73) Assignee: Lundbeck Pharmaceuticals Italy S.P.A., Padua (IT)

( * ) Notice: Subject to any disclaimer, the term of this patent is extended or adjusted under 35 U.S.C. 154(b) by 273 days.

(21) Appl. No.: 16/472,476

(22) PCT Filed: Dec. 20, 2017

(86) PCT No.: PCT/EP2017/083804
§ 371 (c)(1),
(2) Date: Jun. 21, 2019

(87) PCT Pub. No.: WO2018/115116
PCT Pub. Date: Jun. 28, 2018

(65) Prior Publication Data
US 2021/0130307 A1    May 6, 2021

(30) Foreign Application Priority Data
Dec. 23, 2016 (IT) .......................... 102016000130729

(51) Int. Cl.
*C07D 265/30* (2006.01)
*B01J 23/42* (2006.01)
*B01J 23/44* (2006.01)

(52) U.S. Cl.
CPC ............ *C07D 265/30* (2013.01); *B01J 23/42* (2013.01); *B01J 23/44* (2013.01)

(58) Field of Classification Search
CPC .................................................. C07D 265/30
USPC ........................................................ 544/170
See application file for complete search history.

(56) References Cited

U.S. PATENT DOCUMENTS

| | | | | |
|---|---|---|---|---|
| 4,565,695 A | * | 1/1986 | Guss .................... | A01N 49/00 424/84 |
| 7,902,357 B2 | * | 3/2011 | Artus Surroca ........ | A61P 1/02 544/170 |
| 7,910,730 B2 | * | 3/2011 | Artus Surroca ... | C07D 295/088 544/105 |
| 10,717,747 B2 | | 7/2020 | De Faveri et al. | |
| 10,815,251 B2 | | 10/2020 | De Faveri et al. | |
| 10,894,778 B2 | * | 1/2021 | De Faveri ............ | C07D 265/30 |
| 2016/0016956 A1 | * | 1/2016 | Esaki .................. | A61P 35/00 540/453 |
| 2019/0359632 A1 | | 11/2019 | De Faveri et al. | |
| 2019/0375722 A1 | | 12/2019 | De Faveri et al. | |
| 2020/0181167 A1 | | 6/2020 | De Faveri et al. | |

FOREIGN PATENT DOCUMENTS

| | | |
|---|---|---|
| EP | 0 038 785 B1 | 11/1985 |
| WO | WO 90/14342 A1 | 11/1990 |
| WO | WO 2006/120432 A1 | 11/2006 |
| WO | WO 2007/010294 A2 | 1/2007 |
| WO | WO 2007/057681 A1 | 5/2007 |
| WO | WO 2007/091009 A2 | 8/2007 |
| WO | WO 2007/099302 A2 | 9/2007 |
| WO | WO 2008/139170 A2 | 11/2008 |
| WO | WO 2012/131363 A2 | 10/2012 |

OTHER PUBLICATIONS

Surroca, U.S. Pat. No. 7,902,357, Myrsina, Inst, Org.Chem. 1975, 41, 1068-1070.*
Kossanyi, Tetrahedron Letters (1973), (36), 3459-62.*
Siriwanrdana Tetrahedron Letts, 44 (2003), 985-987.*
U.S. Appl. No. 16/472,367, filed Jun. 21, 2019, Pending.
U.S. Appl. No. 16/472,399, filed Jun. 21, 2019, Pending.
PCT/EP2017/083768, Feb. 20, 2018, International Search Report and Written Opinion.
PCT/EP2017/083795, Mar. 20, 2018, International Search Report and Written Opinion.
PCT/EP2017/083804, Feb. 22, 2018, Invitation to Pay Additional Fees.
PCT/EP2017/083804, Apr. 17, 2019, International Search Report and Written Opinion.
International Search Report and Written Opinion for Application No. PCT/EP2017/083768 dated Feb. 20, 2018. 13 pages.
International Search Report and Written Opinion for Application No. PCT/EP2017/083795 dated Mar. 20, 2018. 13 pages.
Invitation to Pay Additional Fees for Application No. PCT/EP2017/083804 dated Feb. 22, 2018. 10 pages.
International Search Report and Written Opinion dated Apr. 17, 2018 in connection with Application No. PCT/EP2017/083804. 15 pages.
Huang et al., Ring-opening reaction of metyhlenecy clopropanes with LiCl, LiBr, or NaI in acetic acid. Tetrahedron. Feb. 23, 2004;60(9):2057-2062.
Höver et al., Darstellung primärer Alkohole aus verzweigten Olefinen [Preparation of primary alcohols from branched olefins]. Justus Liebigs Ann. Chem. 1965;685:89-96. German language.
Jones et al., Sex attractant of the pink bollworm moth: isolation, identification, and synthesis. Science. Jun. 10, 1966;152(3728):1516-7.
Kossanyi et al., Insect chemistry. Application of the norrish type-I reaction to the synthesis of propylure, the sexual pheromone of *Pectinophora gossypiella saunder*. Tetrahedron Letters. 1973;14(36):3459-3462.
Myrsina et al., Ukrainskii Khimicheskii Zhurnal (Russian Edition) [Synthesis of trans-1-acetoxy-10-(n-Propyl)-trideca-5,9-diene (propylur), sex attractant of cotton moth. Inst Org Chem NASSU]. 1975;41:1068-1070.

(Continued)

*Primary Examiner* — Nizal S Chandrakumar
(74) *Attorney, Agent, or Firm* — Wolf, Greenfield & Sacks, P.C.

(57) ABSTRACT

The present invention relates to a new process for producing intermediates useful in the manufacture of 2-(3-(4-propylheptyl)morpholino)ethan-1-ol. The invention also relates to intermediates 1-chloro-4-propylhept-3-ene and 1-iodo-4-propyl-hept-3-ene.

19 Claims, No Drawings

(56) References Cited

OTHER PUBLICATIONS

Siriwardana et al., Addition of hydrogen halides to alkylidenecyclopropanes: a highly efficient and stereoselective method for the preparation of homoallylic halides. Tetrahedron Letters. Jan. 27, 2001;44(5):985-987.

Studt, $C_{26}$-Kohlenwasserstoffe als Schmieröl-Modellsubstanzen, II [$C_{26}$ hydrocarbons as lubricant oil model substances, II]. Justus Liebigs Ann. Chem. 1966;693:90-98. German language.

Tatemitsu et al., Double- and triple-layered charge transfer cyclophanes containing tetracyanoquinodimethane and dimethoxybenzene groups. Tetrahedron Letters. 1978;19(37):3459-3462.

Yoshida et al., Crucial structural factors and mode of action of polyene amides as inhibitors for mitochondrial NADH-ubiquinone oxidoreductase (complex I). Biochemistry. Sep. 11, 2007;46(36):10365-72. Epub Aug. 9, 2007.

U.S. Appl. No. 16/472,367, filed Jun. 21, 2019, Granted, U.S. Pat. No. 10,894,778.

U.S. Appl. No. 16/472,399, filed Jun. 21, 2019, Granted, U.S. Pat. No. 10,717,747.

U.S. Appl. No. 16/791,245, filed Feb. 14, 2020, Granted, U.S. Pat. No. 10,815,251.

Mori K. New syntheses of 1,7-dimethylnonyl propanoate, the western corn rootworm pheromone, in four different ways via cross metathesis, alkylation and coupling reactions. Biosci Biotechnol Biochem. 2010;74(3):595-600. Epub Mar. 7, 2010.

\* cited by examiner

US 11,384,056 B2

METHOD FOR THE MANUFACTURING OF DELMOPINOL INTERMEDIATES

CROSS REFERENCE TO RELATED APPLICATIONS

This Application is a National Stage filing under 35 U.S.C. 371 of International Patent Application No. PCT/EP2017/083804, filed Dec. 20, 2017, which claims foreign priority benefits under 35 U.S.C. § 119(a)-(d) or 35 U.S.C. § 365(b) of Italian application Number 102016000130729, filed Dec. 23, 2016. The entire contents of these applications are incorporated herein by reference in their entirety.

FIELD OF THE INVENTION

The present invention relates to a process for the manufacture of 2-(3-(4-propylheptyl)morpholino)ethan-1-ol and the manufacture of intermediates useful in said process.

The invention also relates to intermediates in said process, i.e. 1-chloro-4-propylhept-3-ene and 1-iodo-4-propylhept-3-ene.

BACKGROUND OF THE INVENTION

The compound 2-(3-(4-propylheptyl)morpholino)ethan-1-ol (CAS 79874-76-3) having the INN name delmopinol was disclosed for the first time by Ferrosan in EP0038785 and has the molecular structure depicted below.

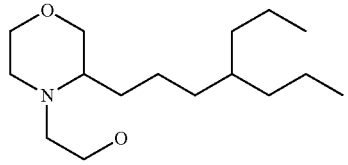 [SMILES: CCCC(CCC)CCCC1COCCN1CCO]

Delmopinol is used in the treatment of gingivitis, prevention of plaque formation and for oral hygiene in general. It is an active component in mouth wash liquids and toothpaste for use in humans and is also used in the maintenance of oral health in animals as described in WO 2007/099302.

Several methods for synthesis of delmopinol have been disclosed (e.g. WO 90/14342 and WO 2007/091009) and an industrially applicable method disclosed in WO 2007/057681. This latter discloses a process where delmopinol is obtained by reaction of oxazolidin[2,3-c]morpholine with a Grignard compound $R_1MgX$ where X is a halogen selected from Cl, Br and I and $R_1$ is an alkyl or aryl moiety. WO 2007/057681 more specifically discloses the reaction of oxazolidin[2,3-c]morpholine with a Grignard reagent prepared from 1-halo-4-propylheptane (in particular 1-bromo-4-propylheptane), to obtain delmopinol.

WO 2007/057681 describes the preparation of 1-halo-4-propylheptane by halogenation of 4-propylheptan-1-ol. In particular, it mentions the preparation of 1-bromo-4-propylheptane by treatment with aqueous hydrogen bromide. The preparation of 4-propylheptan-1-ol is obtained according to *Justus Liebigs Ann. Chem.* 1966, 693, 90-98 describing the synthesis of 4-propylheptan-1-ol in four steps in 58% overall yield from γ-butyrolactone which is a controlled substance with use restrictions. In another process described in *Justus Liebigs Ann. Chem.* 1965, 685, 89-96 4-propylheptan-1-ol is obtained from 4-propylhept-3-ene in a molar yield of only 15%. *Biochemistry* 2007, 46, 10365-10372 reports the preparation of 4-propylheptan-1-ol in three steps from 2-propyl-1-pentanol in 34% overall yield.

The preparation of 4-propylheptan-1-ol using the methods described in the literature is not straightforward and is accomplished through multistep processes. All the methods suffer from low yield, high cost or use of materials which are not commercially available or the use of which is restricted with consequent impact on the overall cost of delmopinol.

Thus, there is a need within the field to find improved processes for the preparation of the intermediate 1-halo-4-propylheptane for producing delmopinol. In particular, there is a need for new methods that are safe and cost-effective and provides 1-halo-4-propylheptane in a quality suitable for the production of delmopinol and are readily applicable on industrial scale.

It is thus within the scope of the present invention to provide a method for the production of 1-halo-4-propylheptane suitable for the use in the manufacturing of highly pure delmopinol.

SUMMARY OF THE INVENTION

In one embodiment, the invention provides a process for manufacturing of delmopinol, which process comprises the use of 1-halo-4-propylhept-3-ene.

In one embodiment, the invention provides a process for the manufacture of delmopinol, in which process 1-halo-4-propylhept-3-ene (IV) is converted to 1-halo-4-propylheptane (V) by catalytic hydrogenation and wherein said 1-halo-propylheptane is subsequently converted to propylheptanemagnesiumhalide, which is further reacted with oxazolidine[2,3-c]morpholine to obtain delmopinol

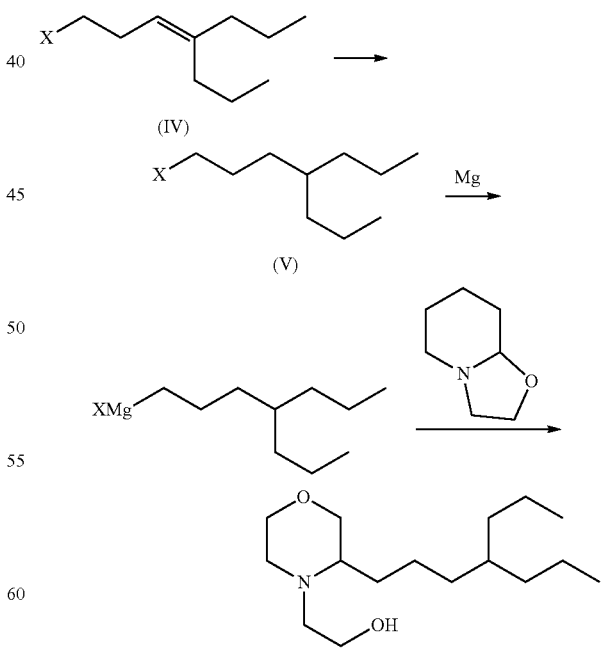

X=Cl, Br or I, optionally followed by reaction with an appropriate acid to obtain a pharmaceutically acceptable salt of delmopinol.

In one embodiment, the invention provides a process for the manufacture of 1-halo-4propylhept-3-ene

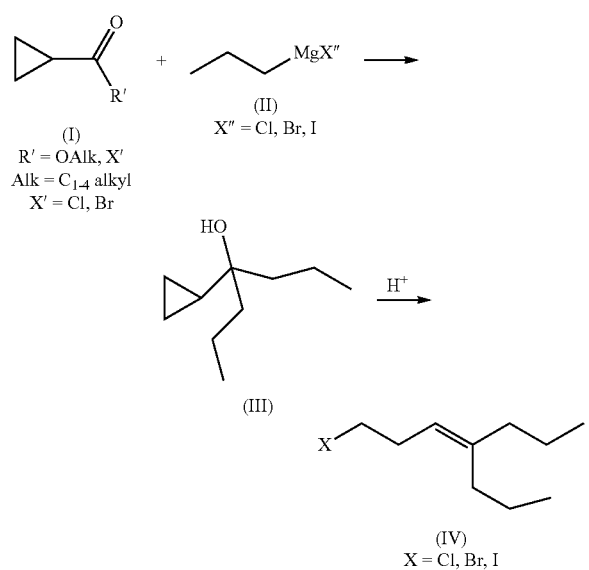

wherein H⁺ is a halogenhydric acid (HX) or a non-halogenhydric acid.

In one embodiment, the invention relates to a pharmaceutical composition, comprising delmopinol, wherein said delmopinol is directly obtained by the process described above. Said pharmaceutical composition can be for human or veterinary use.

The invention further relates to the intermediate 1-chloro-4-propylhept-3-ene and 1-iodo-4-propylhept-3-ene and their use in the manufacturing of Delmopinol.

Definitions

Throughout the application, the term "delmopinol" is intended to include any form of the compound, such as the free base or a pharmaceutically acceptable salt. Particular mention is made of the hydrochloride salt. The free base and pharmaceutically acceptable salts include anhydrous forms and solvated forms such as hydrates. The anhydrous forms and the solvates include amorphous and crystalline forms. The term "delmopinol" encompasses the racemate and the pure enantiomers and mixtures of the enantiomers in any ratio.

In the present context, the term "halo" indicates bromo or chloro or iodo. In a preferred embodiment, "halo" indicates chloro.

In the present context, the compound "1-halo-4-propyl-hept-3-ene" indicates 1-bromo-4-propylhept-3-ene, 1-chloro-4-propylhept-3-ene or 1-iodo-4-propylhept-3-ene.

In the present context, the term "$C_{1-4}$alkyl" indicates an alkyl selected from methyl, ethyl, n-propyl, isopropyl, n-butyl, 1-methylpropyl and 2-methylpropyl. In a preferred embodiment, "$C_{1-4}$alkyl" indicates methyl.

In the present context the term HX indicates a halogenhydric acid such as hydrogen chloride, hydrogen bromide or hydrogen iodide.

In the present context the term "purity" indicates the percentage by area of the product determined by a chromatographic method, such as gas liquid chromatography, GC.

In the present context the term "assay" indicates the percentage by weight of the product in a given mixture determined by e.g. potentiometric titration.

In the present context the term "conversion" indicates the extent of the transformation of a substrate in a given reaction.

In the present context the term "selectivity" indicates the ratio of the desired product vs. the sum of the desired product and the by-products of a given reaction.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid. In one embodiment, a pharmaceutically acceptable salt is formed with hydrochloric acid Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

DETAILED DESCRIPTION OF THE INVENTION

The inventors have found an efficient and cost-effective process for the manufacture of 1-halo-4-propylheptane useful as an intermediate in the production of delmopinol, 2-(3-(4-propylheptyl)morpholino)ethan-1-ol.

In an industrially applicable process for the manufacture of delmopinol 1-halo-4-propylheptane is prepared by halogenation of 4-propylheptan-1-ol (WO 2007/057681). However, the synthesis of the intermediate 4-propylheptan-1-ol has some disadvantages as described in the background section.

The inventors of the present invention found a new and efficient method for manufacturing of the intermediate 1-halo-4-propylheptane (V) going through the intermediate 1-halo-4-propylhept-3-ene (IV) as depicted in scheme 1 below. The inventors have identified hydrogenation conditions that permit to obtain 1-halo-4-propylheptane by reduction of 1-halo-4-propylhept-3-ene with limited dehalogenation, i.e. with high selectivity. The inventors also found that this process is particularly efficient when X is Cl.

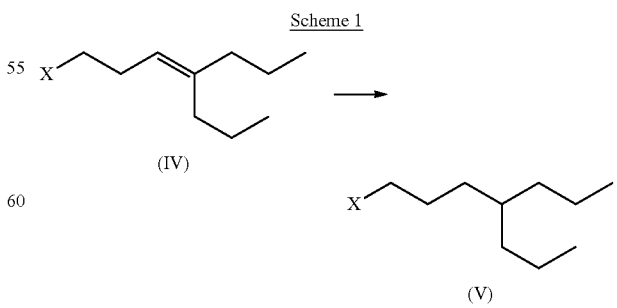

Homoallylic halides in general (like 1-halo-4-propylhept-3-ene) may to be prone to dehalogenation and it would therefore be expected that this route of synthesis would be less attractive.

*Science* 1966, 152, 1516-1517 describes the preparation of 1-bromo-4-propylhept-3-ene from heptan-4-one and ethyl bromoacetate in four steps resulting in an overall yield of only 38%. A more straightforward synthesis of 1-bromo-4-propylhept-3-ene is described in Tetrahedron Letters 1973, 36, 3459-3462 and in *Ukrainskii Khimicheskii Zhurnal* 1975, 41, 1068-1070 wherein 1-bromo-4-propylhept-3-ene was synthesized in two steps and obtained in yields of 80% and 64%. The method comprises the acidic rearrangement of cyclopropyl alcohols obtained by reaction of suitable cyclopropanecarbonyl derivative with propylmagnesium bromide. The process is depicted in scheme 2 below.

Scheme 2

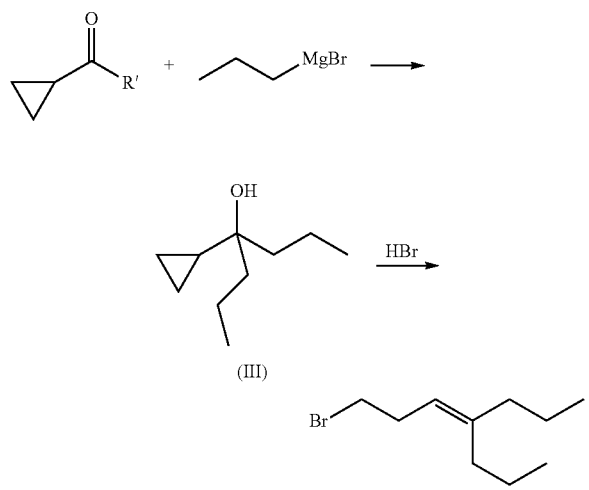

R' = Pr, OEt, OBu, OH, Cl

In addition to the hydrogenation of 1-halo-4-propylhept-3-ene to 1-halo-4-propylheptane, the inventors have found improved conditions for the manufacturing of the 1-halo-4-propylhept-3-ene (IV) according to scheme 3.

Scheme 3

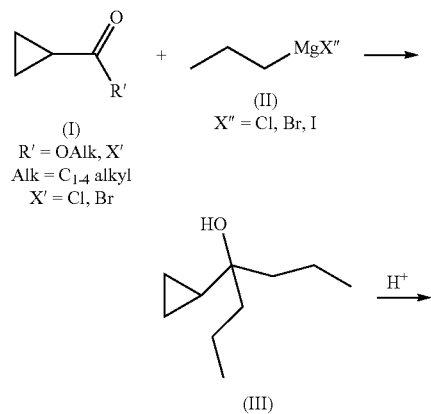

(I)
R' = OAlk, X'
Alk = $C_{1-4}$ alkyl
X' = Cl, Br (II)
X" = Cl, Br, I

-continued (IV)
X = Cl, Br, I wherein $H^+$ is a halogenhydric acid (HX) or a non-halogenhydric acid.

One way to achieve compound (IV) according to scheme 3 is when $H^+$ is a halogenhydric acid such as hydrogen chloride, hydrogen bromide or hydrogen iodide, preferably hydrogen chloride. A cyclopropanecarbonyl derivative (I) is reacted with a propylmagnesium halide (II) to give 4-cyclopropylheptan-4-ol (III). The alcohol (III) is then treated with a suitable halogenhydric acid to afford the desired 1-halo-4-propylhept-3-ene (IV).

Suitable cyclopropanecarbonyl derivatives include $C_{1-4}$alkyl-esters of cyclopropanecarboxylic acid, preferably methyl cyclopropanecarboxylate; and cyclopropylcarbonyl halides, preferably cyclopropanecarbonyl chloride.

The organomagnesium reagent (II) of 1-halopropane, where the halogen is chloro, bromo or iodo, preferably 1-bromopropane or 1-chloropropane, is used in a ratio from 2 to 3 equivalents vs. the carbonyl derivative (I), preferably from 2 to 2.3 equivalents. A suitable solvent for the Grignard coupling include a cyclic and an acyclic ether and a mixture thereof with an alkyl or an aryl hydrocarbon; preferably the reaction is conducted in an ethereal solvent, more preferably the reaction is conducted in tetrahydrofuran (THF).

4-Cyclopropylheptan-4-ol (III) may be isolated from the reaction mixture prior to further processing, which can be done using methods known to the skilled person in the art, and then further reacted with $H^+$ which is a halogenhydric acid HX.

The inventors have found that the transformation can be accomplished using the halogenhydric acid only a small excess thus limiting unwanted side reactions and the wastes and obtaining compound (IV) in a high purity suitable for further processing to Delmopinol.

The transformation of (III) into (IV) is achieved using from 1 to 2 equivalents of halogenhydric acid HX relative to the cyclopropylcarbonyl derivative (I), preferably 1.5 eq. The transformation of (III) into (IV) can be accomplished in an organic solvent such as an ether, a hydrocarbon or an ester or a mixture thereof. Preferably the reaction is run in an ethereal solvent, more preferably the reaction is run in THF. The reaction is conducted at a temperature from 0° C. to reflux until the conversion to 1-halo-propylhept-3-ene is complete.

Another way to achieve 1-halo-4-propylhept-3-ene (IV) according to reaction scheme 3 is when $H^+$ is a non-halogenhydric acid such as sulfuric acid, perchloric acid or fluorosulfuric acid.

Then, in a first embodiment, magnesium 4-cyclopropyl-heptan-4-olate halide, originating from the reaction of the cyclopropylcarbonyl derivative (I) where R is OAlk and propylmagnesium halide (II), is treated with a non-halogenhydric acid such as sulfuric acid, perchloric acid or fluorosulfuric acid, affording directly the desired 1-halo-propyl-hept-3-ene having the same halogen as the starting propylmagnesium halide (II). Suitable cyclopropanecarbonyl derivatives include $C_{1-4}$alkyl-esters of cyclopropanecarboxylic acid, preferably methyl cyclopropanecarboxylate.

In a second embodiment, when the starting materials are a cyclopropylcarbonyl derivative (I) where R is X' and 1-halomagnesiumpropane (II) where X"=X', such treatment with a non halogenhydric acid such as sulfuric acid, perchloric acid or fluorosulfuric acid gives directly 1-halopropylhept-3-ene where X is the same as in the starting materials i.e. X=X'=X". Preferably X=X'=X" is Cl.

The inventors have found that the transformation can be accomplished using the non-halogenhydric acid in only a small excess thus limiting unwanted side reactions and the wastes and obtaining compound (IV) in a high purity suitable for further processing to Delmopinol. The transformation using a non-halogenhydric acid is obtained using from 1 to 2.5 mol of acid per mol of 1-halopropane, preferably from 1 to 2.

Reduction of homoallylic halides to saturated halides is prone to be accompanied by dehalogenation affording the corresponding alkane and halogenhydric acid HX as side products. The formation of the halogenhydric acid is unwanted and of particular concern as it is corrosive for stainless steel equipment.

The inventors have found suitable conditions for catalytic hydrogenation that permit obtaining 1-halo-4-propylheptane (V) by reduction of 1-halo-4-propylhept-3-ene (IV), according to scheme 1, with no or only limited dehalogenation. Reduction of homoallylic halides to saturated halides is usually carried out in a solvent selected among alcohols, ethers, esters, organic acids and mixtures thereof. The inventors have found that the hydrogenation step of the present invention is significantly improved when hydrogenation of 1-halo-4-propylhept-3-ene occurs in an alcohol or an organic acid; preferably the hydrogenation is run in glacial acetic acid. The inventors also found that this process is particularly efficient when X is Cl.

The catalyst can be selected among elements of the Group 10 of the Periodic Table of the Elements, preferably the catalyst is a palladium or platinum based catalyst, most preferred is a palladium based catalyst. The hydrogenation is performed at a temperature from 20 to 60° C., preferably from 30 to 40° C.

Purification of 1-halopropylheptane (V) can be accomplished by methods known to the person skilled in the art, e.g. by distillation.

The quality of 1-halo-propylheptane obtained by the process of this invention is suitable for the use in the synthesis of delmopinol by reaction with oxazolidin[2,3-c]morpholine according to the route of synthesis disclosed in WO 2007/057681.

In one embodiment, the invention provides a process for the manufacture of delmopinol, in which process 1-halo-4-propylhept-3-ene (IV) is converted to 1-halo-4-propylheptane (V) by catalytic hydrogenation and wherein said 1-halopropylheptane is subsequently converted to halomagnesiumpropylheptane, which is further reacted with oxazolidine[2,3-c]morpholine to obtain delmopinol, as depicted in scheme 4 below Scheme 4

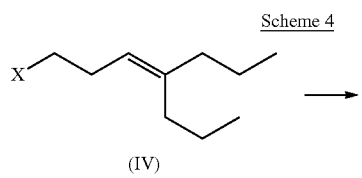

(IV)

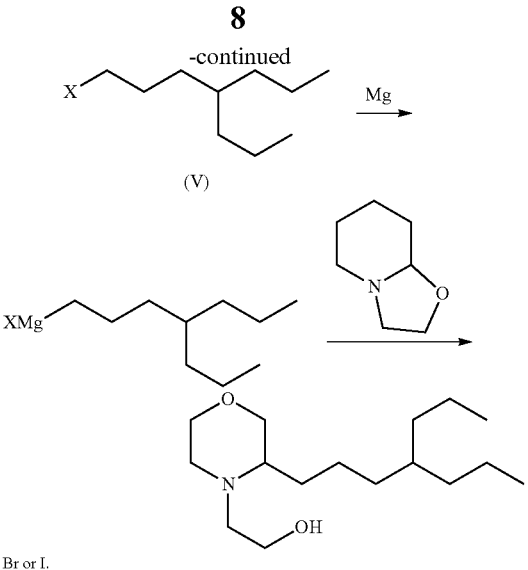

X = Cl, Br or I.

If a pharmaceutically acceptable salt of delmopiniol is desired, reacting delmopinol obtained as described above with an appropriate acid will afford such salt.

In one embodiment, the present invention relates to delmopinol directly obtained by the process described above. In a further embodiment, said delmopinol is purified by distillation, preferably by thin film distillation. In one embodiment the present invention relates to highly pure delmopinol salts prepared by the process described above.

The present invention also relates to a pharmaceutical composition comprising delmopinol obtained by the process of the invention. The pharmaceutical composition may further comprise at least one pharmaceutically acceptable excipient, carrier and/or diluent. Methods for the preparation of pharmaceutical compositions such as liquid pharmaceutical compositions are well known in the art. See, e.g., Remington: The Science and Practice of Pharmacy, 21st ed., Lippincott Williams & Wilkins (2005).

The pharmaceutical composition can be for human use or for veterinary use. Pharmaceutical compositions comprising delmopinol obtained according to the present invention are intended for local administration in the oral cavity.

The pharmaceutical composition for human use is preferably a liquid composition comprising delmopinol in a therapeutically effective amount, preferably as the delmopinol HCl. The pharmaceutical composition can for example be a mouth wash product or a toothpaste. It is envisaged that a pharmaceutical composition for human use comprising delmopinol obtained by a process of the invention may be used for treatment of oral diseases such as gingivitis or for prevention of plaque formation. In one embodiment, the composition may be used for general oral hygiene. Preferably, the pharmaceutical composition for human use comprising delmopinol obtained by the process of the invention is a liquid composition comprising delmopinol HCl in a concentration of 1-5%, such as about 1%, 2%, 3%, 4% or 5%, preferably about 2%. Said pharmaceutical composition is preferably a mouth wash product or a toothpaste.

Pharmaceutical compositions for veterinary use comprising delmopinol have been described in WO 2007/099302. In one embodiment, a pharmaceutical composition for veterinary use is an animal chew wherein the term chew is given its normal meaning in the art and refers to any toy, accessory or foodstuff that is intended for chewing or gnawing by an animal (WO 2007/099302). Preferably, the pharmaceutical composition for veterinary use is for use in the treatment of a pet such as a cat or a dog, most preferably a dog. Further variations of compositions for veterinary use comprising delmopinol has been disclosed in WO 2007/099302 which is incorporated herein by reference.

In one embodiment, the invention relates to a mouth wash product or a toothpaste comprising delmopinol obtained by the process of the invention.

In one embodiment, the invention relates to an animal chew comprising delmopinol obtained by the process of the invention. In a particular embodiment, said animal chew is for use in the treatment of a dog.

In one embodiment, the invention relates to delmopinol obtained by the process of the invention for use in the treatment oral diseases such as gingivitis, or for prevention of plaque formation.

The term "therapeutically effective amount" means an amount sufficient to alleviate, arrest, partly arrest or delay progress of the clinical manifestations of a given disease and its complications in a therapeutic intervention comprising the administration of said compound. An amount adequate to accomplish this is defined as "therapeutically effective amount". It will be understood that determining an appropriate dosage may be achieved using routine experimentation, by constructing a matrix of values and testing different points in the matrix, which is all within the ordinary skills of a trained physician.

In the present context, "treatment" or "treating" is intended to indicate the management and care of a patient for the purpose of alleviating, arresting, partly arresting or delaying progress of the clinical manifestation of the disease. The patient to be treated is preferably a mammal, in particular a human being.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

Embodiments According to the Invention

In the following, embodiments of the invention are disclosed. The first embodiment is denoted E1, the second embodiment is denoted E2 and so forth.

E1. A process for manufacturing of delmopinol, which process comprises the use of 1-halo-4-propylhept-3-ene.

E2. The process according to embodiment 1, wherein said 1-halo-4-propylhept-3-ene (IV) is converted to 1-halo-4-propylheptane (V) by catalytic hydrogenation as depicted in the reaction scheme below

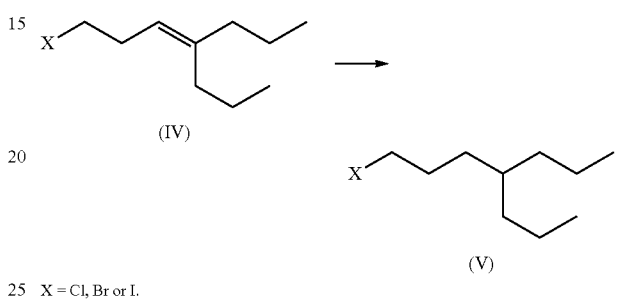

X = Cl, Br or I.

E3. The process according to embodiment 2, wherein said catalytic hydrogenation takes place in an alcohol or an organic acid.

E4. The process according to any of embodiments 2-3, wherein said catalytic hydrogenation takes place in glacial acetic acid.

E5. The process according to any of embodiments 2-4, wherein said catalytic hydrogenation is performed with a catalyst selected from a palladium or platinum based catalyst.

E6. The process according to any of embodiments 2-5, wherein said catalytic hydrogenation is performed at a temperature from 20 to 60° C., such as from 30 to 40° C.

E7. The process according to any of embodiments 1-6, wherein said 1-halo-4-propylhept-3-ene (IV) is converted to 1-halo-4-propylheptane (V) by catalytic hydrogenation and wherein said 1-halo-propylheptane is subsequently converted to delmopinol, as depicted in the reaction scheme below

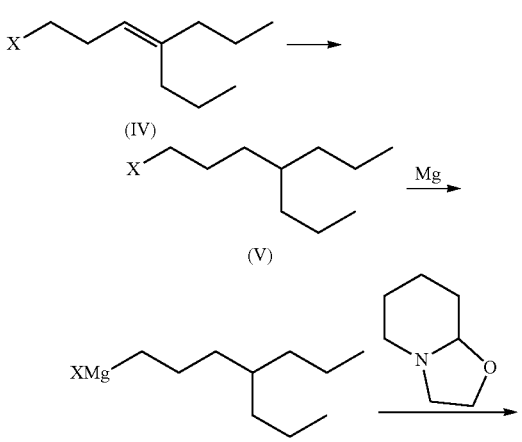

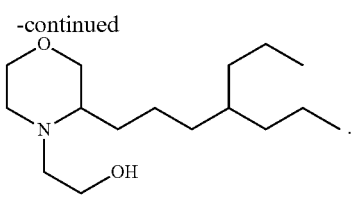

X = Cl, Br or I.

E8. The process according to any of embodiments 2-7, wherein X is Cl.

E9. The process according to any of embodiments 1-8, wherein said 1-halo-4-propylhept-3-ene is prepared according to the process depicted in the reaction scheme below

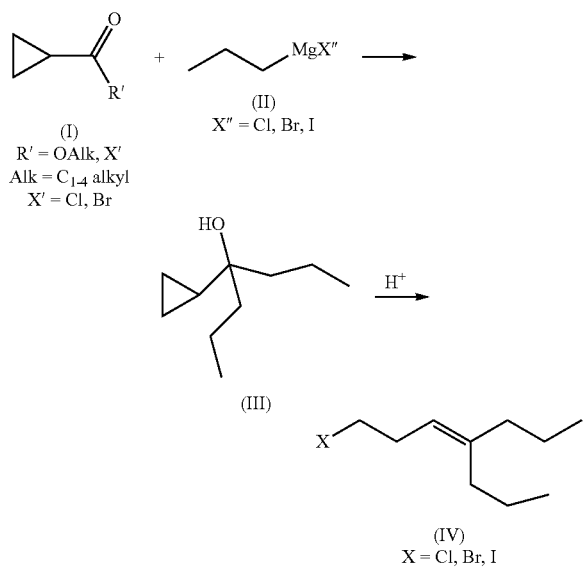

(I)
R' = OAlk, X'
Alk = C$_{1-4}$ alkyl
X' = Cl, Br (III)

(IV)
X = Cl, Br, I wherein H$^+$ is a halogenhydric acid (HX) or a non-halogenhydric acid.

E10. A process for the manufacture of 1-halo-4-propylhept-3-ene as depicted in the reaction scheme below

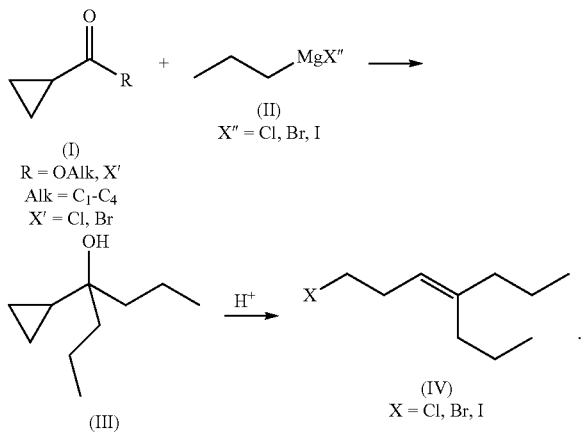

(I)
R = OAlk, X'
Alk = C$_1$-C$_4$
X' = Cl, Br (III)

(IV)
X = Cl, Br, I wherein H$^+$ is a halogenhydric acid which is used in an amount of 1 to 2 equivalents of relative to the cyclopropanecarbonyl derivative (I), preferably about 1.5 equivalents, or wherein H$^+$ is a non halogenhydric acid used in an amount of 1 to 2.5 mol of acid such as 1 to 2 mol of acid per mol of 1-halopropane.

E11. The process according to any of embodiments 9-10, wherein R is —O-methyl.

E12. The process according to any of embodiments 2-11, wherein X is Cl.

E13. The process according to any of embodiments 9-10 and 12, wherein R is X' and X' is Cl.

E14. The process according to any of embodiments 9-13, wherein X" is Cl or Br.

E15. The process according to any of embodiments 9-14, wherein 4-cyclopropylheptan-4-ol (III) is isolated from the reaction mixture prior to further processing and H$^+$ is a halogenhydric acid.

E16. The process according to any of embodiments 9-15, wherein H$^+$ is a halogenhydric acid selected from hydrogen chloride and hydrogen bromide.

E17. The process according to embodiment 16, wherein H$^+$ is hydrogen chloride.

E18. The process according to any of embodiments 9-17, wherein (I) is selected from methylcyclopropane carboxylate and cyclopropanecarbonyl chloride.

E19. The process according to any of embodiments 9-18, wherein the transformation of (III) to (IV) is achieved using from 1 to 2 equivalents of halogenhydric acid HX relative to the cyclopropanecarbonyl derivative (I), preferably about 1.5 equivalents.

E20. The process according to any of embodiments 9-19, wherein the transformation of (III) into (IV) takes place in an organic solvent such as an ether, a hydrocarbon or an ester or a mixture thereof.

E21. The process according to any of embodiments 9-20, wherein the transformation of (III) into (IV) takes place in THF.

E22. The process according to any of embodiments 9-21, wherein the transformation of (III) into (IV) takes place at a temperature in the range of 0° C. to reflux.

E23. The process according to any of embodiments 9-14, wherein 4-cyclopropylheptan-4-ol (III) is not isolated from the reaction mixture prior to further processing, and wherein H$^+$ is a non-halogenhydric acid.

E24. The process according to any of embodiments 9-23, wherein (II) is used in a ratio in the range of 2 to 3 equivalents relative to (I) such as in a ratio in the range of 2.0 to 2.3 equivalents.

E25. The process according to any of embodiments 9-24, wherein the Grignard coupling is performed in THF.

E26. The process according to any of embodiments 23-25, wherein R=OAlk, and wherein the mixture of cyclopropanecarboxylic ester (I) and propylmagnesium halide (II) is treated with a non halogenhydric acid obtaining a 1-halopropylhept-3-ene having the same halogen as the starting propylmagnesium halide (II).

E27. The process according to any of embodiments 23-25, wherein R=X', and wherein X'=X", and wherein the mixture of a cyclopropanecarbonyl halide (I) and propylmagnesium halide (II) is treated with a non halogenhydric acid giving 1-halopropylhept-3-ene having the same halogen as (I) and (II).

E28. The process according to any of embodiments 23-27 wherein said non-halogenhydric acid is selected from sulfuric acid, perchloric acid and fluorosulfuric acid.

E29. The process according to any of embodiments 9-14 and 23-28 wherein the non-halogenhydric acid is used in a ratio of 1 to 2.5 mol of acid per mol of 1-halopropane, preferably from 1 to 2.

E30. The process according to any of embodiments 1-9 or 11-29, wherein the obtained delmopinol is purified by distillation, such as thin film distillation.

E31. The process according to any of embodiments 1-30, wherein said delmopinol is further reacted with HCl to obtain delmopinol in the form of the hydrochloride salt.

E32. The process according to any of embodiments 1-9 or 11-30, wherein said delmopinol is obtained in the form of a hydrochloride salt in a purity of at least 98.5% such as at least 99.0%, such as at least 99.5, 99.6, 99.7, 99.8 or 99.9% (A % GC (method 2)).

E33. Delmopinol obtained from the process according to any of embodiments 1-9 or 11-32.

E34. Delmopinol according to embodiment 33, wherein said delmopinol is a hydrochloride salt which is obtained in a purity of at least 98.5% such as at least 99.0%, such as at least 99.5, 99.6, 99.7, 99.8 or 99.9% (A % GC (method 2)).

E35. A pharmaceutical composition, comprising delmopinol obtained from the process according to any of embodiments 1-9 or 11-32.

E36. The pharmaceutical composition according to embodiment 35, wherein said pharmaceutical composition is for human use.

E37. The pharmaceutical composition according to embodiment 35, wherein said pharmaceutical composition is for veterinary use.

E38. The pharmaceutical composition according to any of embodiments 35-37, wherein said pharmaceutical composition is a mouth wash product or a toothpaste.

E39. The pharmaceutical composition according to embodiment 37, wherein said pharmaceutical composition is an animal chew.

E40. A mouth wash product or a toothpaste comprising delmopinol obtained from the process according to any of embodiments 1-32.

E41. An animal chew comprising delmopinol obtained from the process according to any of embodiments 1-9 or 11-32.

E42. Delmopinol obtained from the process according to any of embodiments 1-9 or 11-32 for use in the treatment of an oral disease such as gingivitis, or for prevention of plaque formation.

E43. A method of the treatment of an oral disease such as gingivitis, or for prevention of plaque formation, which method comprises the administration of a therapeutically effective amount of delmopinol obtained from the process according to any of embodiments 1-9 or 11-32.

E44. Use of delmopinol obtained from the process according to any of embodiments 1-9 or 11-32.for the manufacture of a medicament for the treatment of an oral disease such as gingivitis, or for prevention of plaque formation.

E45. The use of delmopinol obtained from the process according to any of embodiments 1-9 or 11-32 in the manufacturing of a medicament for use in the treatment of an oral disease such as gingivitis, or for prevention of plaque formation.

E46. The compound 1-chloro-4-propylhept-3-ene represented by the formula

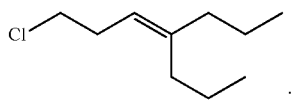

E47. The compound 1-iodo-4-propylhept-3-ene represented by the formula

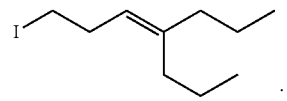

E48. The use of the compound 1-halo-4-propylhept-3-ene in a process for the manufacturing of delmopinol, E49. The use according to embodiment 48, wherein said 1-halo-4-propylhept-3-ene is 1-chloro-4-propylhept-3-ene.

E50. The use according to embodiment 48, wherein said 1-halo-4-propylhept-3-ene is 1-bromo-4-propylhept-3-ene.

E51. The use according to embodiment 48, wherein said 1-halo-4-propylhept-3-ene is 1-iodo-4-propylhept-3-ene.

EXAMPLES

The invention will be illustrated by the following non-limiting examples.

Gas Liquid Chromatography (GC)

| GC method 1 | |
|---|---|
| Column | Restek Rtx-5 amine; 30m, I.D.: 250 μm, F.T.: 0.5 μm (or equivalent) |
| Oven temperature | 110° C. for 0 minutes |
| | 5° C./min ramp to 200° C. |
| | 10° C./min ramp to 315° C. |
| | 300° C. for 10 minutes |
| Carrier | Helium @ 1.0 ml/min |
| Injector temperature | 290° C. (split mode) |
| Split ratio | 20:1 |
| Detector | FID @300° C. |
| Gas to detector | Air (400 ml/min) |
| | $H_2$(40 ml/min) |
| | Make-up: $N_2$ (20 ml/min) |
| Injection volume | 1.0 μl |
| Run Time | 39.5 minutes |
| GC method 2 | |
| Column | DB-WAX; 30m, I.D.: 530 μm, F.T.: 1.0 μm |
| Oven temperature | 100° C. for 5 minutes |
| | 5° C./min ramp to 240° C. |
| | 240° C. for 15 minutes |
| Carrier | Helium @ 8.0 ml/min |
| Injector temperature | 250° C. (split mode) |
| Split ratio | 5:1 |
| Detector | FID @290° C. |
| Gas to detector | Air (400 ml/min) |
| | H2(40 ml/min) |
| | Make-up: N2 (20 ml/min) |
| Injection volume | 1.0 μl |
| Run Time | 48 minutes |

Nuclear Magnetic Resonance (NMR)

$^1$H-NMR spectrum was recorded at 20° C. on a Bruker Avance 300, operating at 300 MHz for $^1$H. Chemical shifts were reported relative to residual deuterated solvent peaks.

Potentiometric Titration Potentiometric titration was carried out in glacial acid using 0.1N $HClO_4$ as titrant Example 1 Preparation of 4-cyclopropylheptan-4-ol In a 1 l reactor magnesium (52.9 g) and THF (162 ml) were charged. A solution of 1-bromopropane (270.3 g) in THF (541 ml) was prepared in a separate vessel. An aliquot of 15 g of that solution was added to the magnesium observing the initiation of the reaction. The remaining amount of solution was added over 30 minutes. The mixture was refluxed for 3 hours and cooled to 20-25° C. A solution of methylcyclopropane carboxylate (100 g) in THF (30 ml) was added to the above n-propylmagnesium bromide in THF over 2.5 hours while keeping the temperature in the range 24-28° C. The mixture was stirred for 5.5 hours and cooled to 0° C. and poured into a solution of ammonium chloride (153 g) in water (612 ml) at T<20° C. The mixture was treated with glacial acetic acid (100 ml) and water (100 ml) and filtered. The layers were separated and the upper layer was concentrated to residue affording 4-cyclopropylheptan-4-ol (150 g) as yellowish oil. Yield 91%, purity 95.0% A (GC method 1).

Example 2 Preparation of 1-chloro-4-propylhept-3-ene

To a mixture of magnesium turnings (kg 10.6) and THF (kg 30.2) at T=40-45° C. a solution of 1-bromopropane (kg 54.1) in THF (kg 100.6) was added. The mixture was then maintained at reflux for 2 hours. The mixture was cooled to 25° C. A solution of methylcyclopropanecarboxylate (kg 20) in THF (kg 5.2) was added over 4 hours to the solution of n-propylmagnesium bromide in THF at T=24-28° C. The dosing vessel was rinsed with THF (5.2 kg). The mixture was stirred at T=24-28° C. for 4 hours and was poured into a solution of ammonium chloride (kg 32) in water (kg 224) keeping the temperature below 20° C. After washing the feed line with THF (kg 17.8) the mixture was treated with glacial acetic acid (kg 21). The mixture was heated to 35° C. and the water layer was separated. The organic solution was concentrated to a final volume of about 90 l. To this solution was added HCl 37% (kg 28.4) at a temperature below 30° C. The mixture was heated to 40° C. for 10 hours and was cooled to T=20-25° C. and diluted with toluene (kg 26). The layers were settled and the water layer was separated. The organic solution was washed with water (kg 30) and with a solution of sodium bicarbonate in water (0.5 kg in 30 kg of water). The solvent was removed obtaining an oil which was distilled under vacuum affording 25.6 Kg of 1-chloro-4-propylhept-3-ene. Yield 69%, purity 94.2% A (GC method 1). $^1$HNMR (dmso-d6): δ=0.84 (t, 3H, $CH_3$), 0.86 (t, 3H, $CH_3$), 1.36 (m, 4H, $CH_2$), 1.94 (t, 2H, $CH_2$), 1.96 (t, 2H, $CH_2$), 2.43 (q, 2H, $CH_2$), 3.58 (t, 2H, $CH_2Cl$), 5.13 (t, 1H, CH).

Example 3 Preparation of 1-chloro-4-propylhept-3-ene

A mixture of magnesium (98.06 g) and THF (192 ml) was heated to 40-45° C. A solution of 1-chloropropane (320 g) in THF (640 ml) was added dropwise at T=50-55° C. over 3.5 hours. The mixture was subsequently heated to reflux for two hours and then cooled to 20° C. To n-propylmagnesium chloride a solution of cyclopropanecarbonyl chloride (193.6 g) in THF (194 ml) was charged over 6.5 hours while keeping T=20-25° C. During the addition the mixture was diluted with THF (300 ml). The mixture was stirred for 18 hours and then it was added to $H_2SO_4$ 36% (1155 g) over three hours maintaining the temperature in the range T=25-30° C. After stirring at the same temperature for 10 hours, the mixture was diluted with toluene (280 ml) and water (500 ml). The organic phase was separated and the aqueous layer was treated with toluene (300 ml). To the collected organic layers were added water (500 ml) and sodium bicarbonate. The organic layer was separated and concentrated to residue. The oil was purified by distillation at T=72-90° C. and P=1-2 mbar yielding 210 g of 1-chloro-4-propylhept-3-ene. Yield 65%, purity 95.9% A (GC method 1).

Example 4 Preparation of 1-bromo-4-propylhept-3-ene

To a mixture of magnesium turnings (24.9 g) and THF (77 ml) was added a solution of 1-bromopropane (130 g) in THF (275 ml) while the temperature increased to reflux. When the addition was complete the mixture was maintained at reflux for one hour and cooled to T=20° C. To n-propylmagnesium bromide in THF a solution of methylcyclopropanecarboxylate (48.1 g) in THF (48 ml) was added over 3 hours. The dosing vessel was washed with THF (20 ml). The resulting mixture was quenched into $H_2SO_4$ 36% (575 g) at T=0-5° C. After diluting with THF (40 ml) the temperature was raised to 20° C. and the mixture was further diluted with toluene (140 ml). The upper layer was separated and the bottom layer was treated with toluene (200 ml) and water (100 ml). The water layer was further diluted with water (150 ml) and extracted with toluene (100 ml). The organic layers were collected and washed with $NaHCO_3$ 5% in water (250 ml) and concentrated to residue yielding 84.2 g of 1-bromo-4-propylhept-3-ene. Yield 76%, purity 94.7% A (GC method 1).

Example 5 Preparation of 1-bromo-4-propylhept-3-ene

4-Cyclopropylheptan-4-ol (25 g) obtained following the procedure reported in Example 1 was mixed with HBr 48% (40.4 g). The mixture was heated to 40° C. and after seven hours further HBr 48% (13.5 g) was added. Further stirring at 40° C. completed the formation of 1-bromo-4-propylhept-3-ene. The mixture was diluted with toluene (50 ml), the organic layer was separated, washed with water (50 ml) and $NaHCO_3$ 5% aqueous solution (25 ml). The organic solution was concentrated to residue obtaining 1-bromo-4-propylhept-3-ene (32.4 g, yield 87%, purity 94.5% A (GC method 1).

Example 6 Purification of 1-chloro-4-propylhept-3-ene

1-Chloro-4-propylhept-3-ene obtained by treating a solution of cyclopropylheptan-4-ol in THF with hydrochloric acid, followed by extraction with toluene and washing with aqueous $NaHCO_3$, was purified by distillation at T=65° C. and P=8 mbar obtaining the target compound with purity of 97.0% A (GC method 1).

Example 7 Purification of 1-bromo-4-propylhept-3-ene

1-Bromo-4-propylhept-3-ene, obtained by treating the mixture obtained from the reaction of propylmagnesium bromide with methylcyclopropane carboxylate with hydrobromic acid, was purified by fractional distillation at T=80° C. and P=28 mbar obtaining the target compound with purity of 96.0% A (GC method 1).

Example 8 Preparation of 1-chloro-4-propylheptane

1-Chloro-4-propylhept-3-ene (10 g) obtained according to Example 3 was hydrogenated at T=30° C., $H_2$ P=3 bar in methanol (50 ml) in the presence of Pt/C 5% (0.5 g) yielding to 1-chloro-4-propylheptane with 100% conversion and 89% selectivity reduction vs. dehalogenation.

Example 9 Preparation of 1-chloro-4-propylheptane

A mixture of 1-chloro-4-propylhept-3-ene (150 g), glacial acetic acid (450 ml) and Pd/C 5% (7.5 g) was hydrogenated at T=30° C. and $H_2$ P=3 bar (98.3% conversion and 100% selectivity). When the hydrogen uptake was finished the catalyst was filtered and washed with glacial acetic acid (50 ml). The solution was concentrated to residue yielding 1-chloro-4-propylheptane (130 g, purity 90% A, GC method 1).

Example 10 Preparation of 1-bromo-4-propylheptane

A mixture of 1-bromo-4-propylhept-3-ene (12.54 g), methanol (188 ml) and Pd/C 5% (0.73 g) was hydrogenated at T=30° C. and $H_2$ P=3 bar yielding to 1-bromo-4-propylheptane with 100% conversion and 82.5% selectivity reduction vs. dehalogenation.

Example 11 Purification of 1-chloro-4-propylheptane 1-chloro-4-propylheptane obtained in Example 9 was distilled at T=63-67° C. and P=0.03-0.04 mbar obtaining 105.2 g of 1-chloro-4-propylheptane (purity 94.7% A, GC method 1).

Example 12 Preparation of 2-(3-(4-propylheptyl)morpholino)ethan-1-ol

To a mixture of magnesium (19.35 g), THF (63 ml) heated to T=50-55° C. was added 1-bromoethane (0.5 g) to initiate the reaction. A solution of 1-chloro-4-propylheptane (142.5 g, purity 92.8% A GC method 1) obtained as described in Example 9 in THF (165 ml) was added over 1.5 hours at T=60-65° C. The mixture was refluxed for two hours and cooled to T=20° C. obtaining 4-propylheptylmagnesium chloride in THF.
To the Grignard reagent of 1-chloro-4-propylheptane a solution of oxazolidin[2,3-c]morpholine 24% w/w in toluene (434 g) was added while keeping the temperature at T=0-5° C. The mixture was stirred at T=5° C. overnight and was poured into a solution of $NH_4Cl$ (56.1 g) in water (392 ml) while keeping the temperature below 15° C. The mixture was treated with glacial acetic acid (60 ml). The organic layer was separated and washed with water (50 ml). The organic layer was concentrated to residue yielding 2-(3-(4-propylheptyl)morpholino)ethan-1-ol, 152 g, assay 57.4% w/w, purity 91.2% A (GC method 2), yield 40%.

Example 13 Purification of 2-(3-(4-propylheptyl)morpholino)ethan-1-ol by Distillation 2-(3-(4-propylheptyl)morpholino)ethan-1-ol obtained in Example 12 was purified by distillation at T=160° C. and P=0.023 mbar obtaining 79.2 g of product as oil having a purity of 95.1% A (GC method 2).

Example 14 Preparation of Delmopinol HCl

Purified 2-(3-(4-propylheptyl)morpholino)ethan-1-ol obtained in Example 13 was dissolved in isopropyl acetate and treated with hydrogen chloride at T=0° C. Precipitation was initiated by seeding. The suspension was stirred at T=0° C. overnight and the solid was isolated by filtration, washed with precooled isopropylacetate and dried under vacuum to yield delmopinol hydrochloride (67.5 g, yield 75%, purity 99.19% A, GC method 2)

The invention claimed is:

1. A process for manufacturing of delmopinol, which process comprises the use of 1-halo-4-propylhept-3-ene,
wherein said 1-halo-4-propylhept-3-ene (IV) is converted to 1-halo-4-propylheptane (V) by catalytic hydrogenation

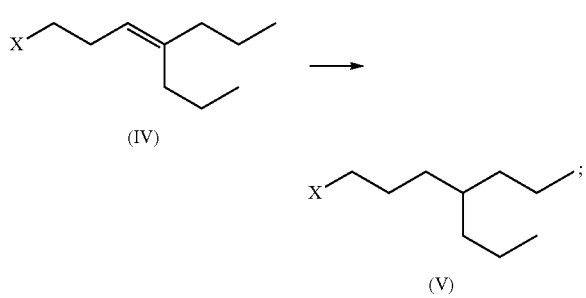

X = Cl;

wherein the catalytic hydrogenation takes place in an alcohol or an organic acid.

2. The process according to claim 1, wherein said catalytic hydrogenation is performed with a catalyst selected from the group consisting of a palladium based catalyst and a platinum based catalyst.

3. The process according to claim 1, wherein said catalytic hydrogenation is performed at a temperature from 20 to 60° C.

4. The process according to claim 1, wherein said 1-halo-4-propylhept-3-ene (IV) is converted to 1-halo-4-propylheptane (V) by catalytic hydrogenation and wherein said 1-halo-propylheptane is subsequently converted to halomagnesiumpropylheptane, which is further reacted with oxazolidine[2,3-c]morpholine to obtain delmopinol

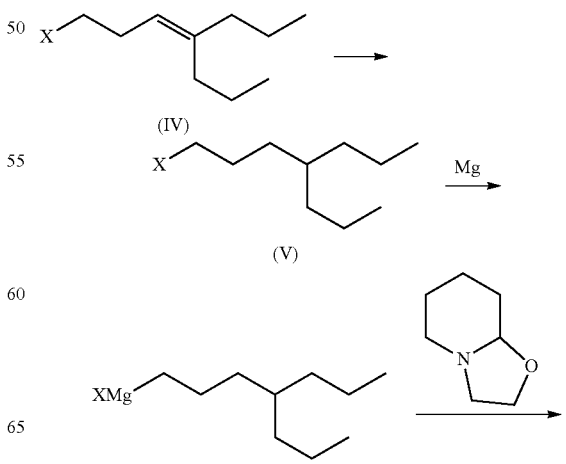

-continued

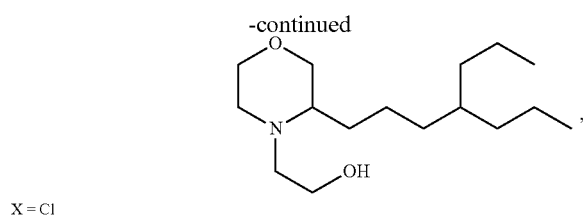

X = Cl which is optionally followed by reaction with an appropriate acid to obtain a pharmaceutically acceptable salt of delmopinol.

5. The process according to claim 1, wherein said 1-halo-4-propylhept-3-ene is prepared according to the process depicted below

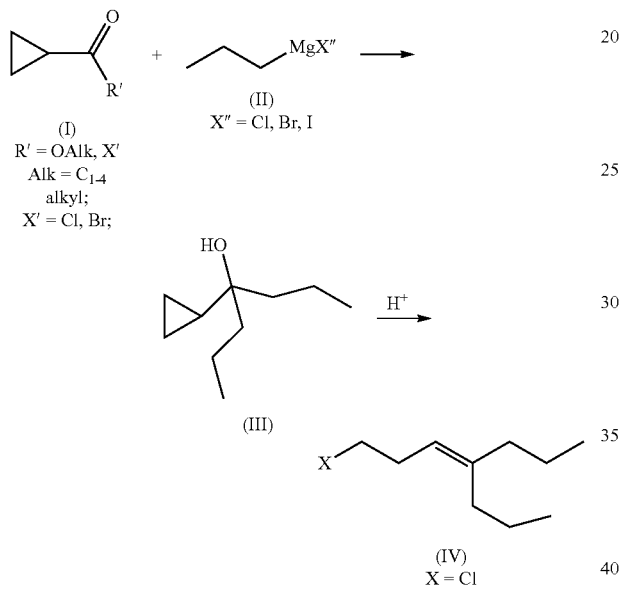

wherein
H⁺ is a halogenhydric acid (HX) or a non-halogenhydric acid.

6. The process according to claim 5, wherein R' is —O-methyl.

7. The process according to claim 5, wherein R' is X'.

8. The process according to claim 5, wherein X" is Cl or Br.

9. The process according to claim 5, wherein 4-cyclopropylheptan-4-ol (III) is isolated from the reaction mixture prior to further processing and H⁺ is a halogenhydric acid.

10. The process according to claim 5, wherein 4-cyclopropylheptan-4-ol (III) is not isolated from the reaction mixture prior to further processing, and wherein H⁺ is a non-halogenhydric acid.

11. The process according to claim 10, wherein R=OAlk, and wherein the mixture of cyclopropanecarboxylic ester (I) and propylmagnesium halide (II) is treated with a non halogenhydric acid obtaining a 1-halo-propylhept-3-ene having the same halogen as the starting propylmagnesium halide (II).

12. The process according to claim 10, wherein R=X', and wherein X'=X", and wherein the mixture of a cyclopropanecarbonyl halide (I) and propylmagnesium halide (II) is treated with a non halogenhydric acid giving 1-halopropylhept-3-ene having the same halogen as (I) and (II).

13. The process according to claim 2, wherein said 1-halo-4-propylhept-3-ene (IV) is converted to 1-halo-4-propylheptane (V) by catalytic hydrogenation and wherein said 1-halo-propylheptane is subsequently converted to halomagnesiumpropylheptane, which is further reacted with oxazolidine[2,3-c]morpholine to obtain delmopinol

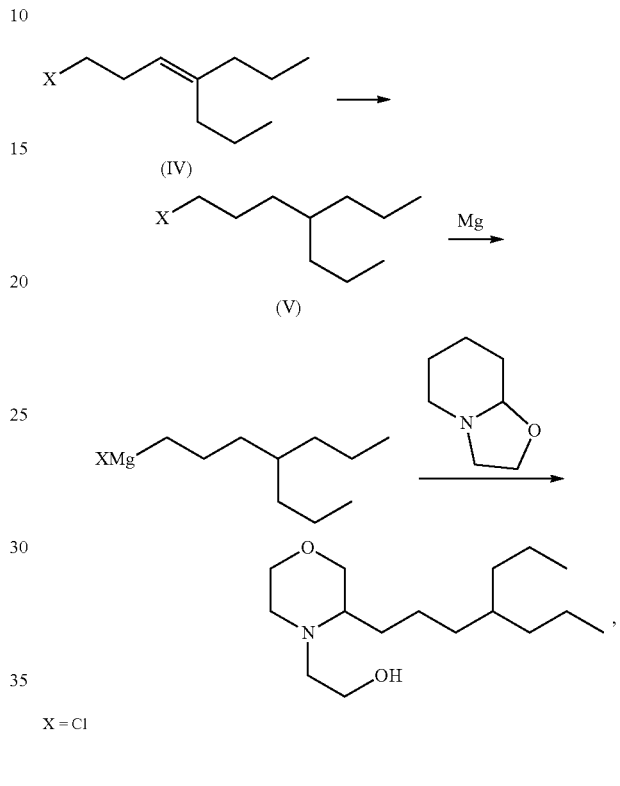

X = Cl which is optionally followed by reaction with an appropriate acid to obtain a pharmaceutically acceptable salt of delmopinol.

14. The process according to claim 2, wherein said 1-halo-4-propylhept-3-ene is prepared according to the process depicted below

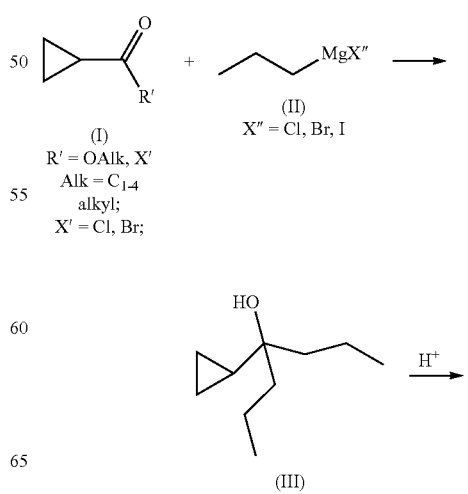

-continued

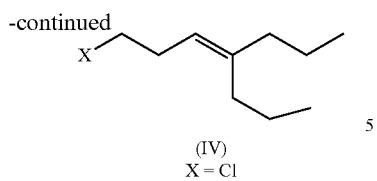

(IV)
X = Cl wherein
wherein $H^+$ is a halogenhydric acid (HX) or a non-halogenhydric acid.

15. The process according to claim 3, wherein said catalytic hydrogenation is performed at a temperature from 30 to 40° C.

16. The process according to claim 1, wherein the alcohol is methanol.

17. The process according to claim 1, wherein the organic acid is glacial acetic acid.

18. The process according to claim 1, wherein said catalytic hydrogenation is performed with a palladium based catalyst.

19. The process according to claim 1, wherein said catalytic hydrogenation is performed with a platinum based catalyst.

\* \* \* \* \*